United States Patent
Taniguchi

(10) Patent No.: US 12,303,410 B2
(45) Date of Patent: *May 20, 2025

(54) STENT DEVICE WITH STENT COVERING WITH REGIONS OF DIFFERING POROSITY

(71) Applicant: OLYMPUS MEDICAL SYSTEMS CORP., Tokyo (JP)

(72) Inventor: Hirofumi Taniguchi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/420,909

(22) Filed: Jan. 24, 2024

(65) Prior Publication Data

US 2024/0164919 A1 May 23, 2024

Related U.S. Application Data

(63) Continuation of application No. 17/673,098, filed on Feb. 16, 2022, now Pat. No. 11,925,571.

(Continued)

(51) Int. Cl.
*A61F 2/90* (2013.01)
*A61F 2/00* (2006.01)
(Continued)

(52) U.S. Cl.
CPC .............. *A61F 2/90* (2013.01); *A61F 2/9517* (2020.05); *A61F 2/962* (2013.01);
(Continued)

(58) Field of Classification Search
CPC .......... A61F 2/90; A61F 2/9517; A61F 2/962; A61F 2002/0081; A61F 2230/0069; A61F 2250/0023

See application file for complete search history.

(56) References Cited

U.S. PATENT DOCUMENTS 5,769,884 A * 6/1998 Solovay ................ A61F 2/07
623/1.13
2002/0052649 A1 5/2002 Greenhalgh
(Continued)

FOREIGN PATENT DOCUMENTS

JP 11-197252 A 7/1999
JP 11-299901 A 11/1999
(Continued)

OTHER PUBLICATIONS

International Search Report dated Apr. 12, 2022, issued in corresponding International Patent Application No. PCT/JP2022/007780.

(Continued)

*Primary Examiner* — Katherine H Schwiker
*Assistant Examiner* — Zehra Jaffri
(74) *Attorney, Agent, or Firm* — Morgan, Lewis & Bockius LLP

(57) ABSTRACT

A stent device including a stent cover having differing porosity ratio is disclosed. The stent covers the stent body comprising of stent wires and stent cells enclosed by the stent wires. The stent cover differs in porosity ratio for areas covering the stent wires and the areas covering the stent cells. The porosity ratio for areas covering the stent wires may have a higher porosity rate in order to promote endothelialization of the stent device. A bilayer stent cover differing in porosity ratio may be used to cover the stent body, as well as stent cover not covering the entirety of the stent body.

20 Claims, 11 Drawing Sheets

Related U.S. Application Data

(60) Provisional application No. 63/153,453, filed on Feb. 25, 2021.

(51) Int. Cl.
*A61F 2/95* (2013.01)
*A61F 2/962* (2013.01)

(52) U.S. Cl.
CPC ............... *A61F 2002/0081* (2013.01); *A61F 2230/0069* (2013.01); *A61F 2250/0023* (2013.01)

(56) References Cited

U.S. PATENT DOCUMENTS

| | | |
|---|---|---|
| 2002/0143384 A1 | 10/2002 | Ozasa |
| 2005/0110214 A1 | 5/2005 | Shank et al. |
| 2006/0217799 A1* | 9/2006 | Mailander ................ A61F 2/91 623/1.44 |
| 2009/0024204 A1 | 1/2009 | Greenhalgh et al. |
| 2011/0137400 A1 | 6/2011 | Dorn et al. |
| 2012/0323309 A1* | 12/2012 | Cattaneo ................ A61F 2/915 623/1.24 |
| 2013/0166017 A1 | 6/2013 | Cartledge et al. |
| 2014/0296957 A1* | 10/2014 | Janzten ................ A61L 31/16 623/1.2 |
| 2015/0196382 A1 | 7/2015 | Richter |
| 2016/0000533 A1 | 1/2016 | Rodriguez Rius et al. |
| 2018/0116781 A1* | 5/2018 | Barone ................ A61F 2/958 |
| 2020/0121482 A1 | 4/2020 | Spector et al. |

FOREIGN PATENT DOCUMENTS

| | | |
|---|---|---|
| JP | 2015-513931 A | 5/2015 |
| JP | 2018-161163 A | 10/2018 |
| JP | 2020-121158 A | 8/2020 |
| JP | 2020-536711 A | 12/2020 |
| WO | 2013/138789 A1 | 9/2013 |
| WO | 2019/074869 A1 | 4/2019 |
| WO | 2019/175341 A1 | 9/2019 |

OTHER PUBLICATIONS

Office Action dated Jul. 19, 2023, issued in related U.S. Appl. No. 17/673,098.
Notice of Allowance dated May 14, 2024, issued in corresponding Japanese Patent Application No. 2023-550224.
Extended European Search Report dated Jan. 8, 2025 issued in corresponding European Patent Application No. 22759777.0.

* cited by examiner

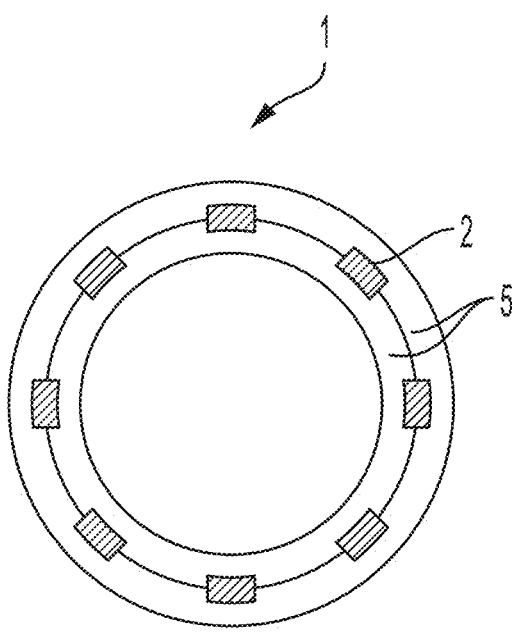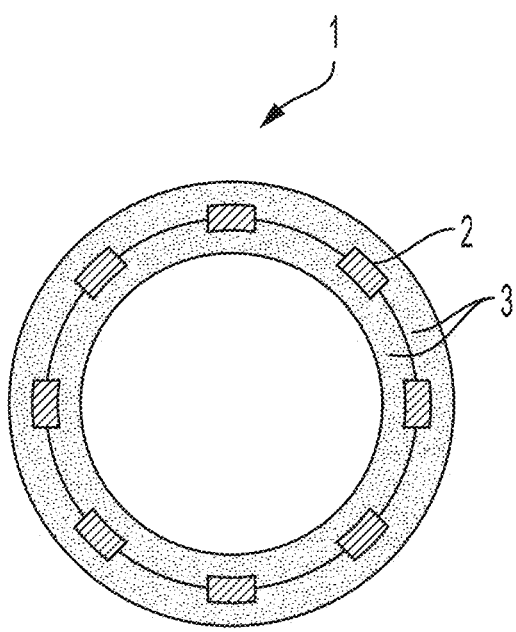
FIG. 15A
(PRIOR ART)
FIG. 15B
(PRIOR ART)

STENT DEVICE WITH STENT COVERING WITH REGIONS OF DIFFERING POROSITY

RELATED APPLICATION DATA

This application is a continuation application of U.S. application Ser. No. 17/673,098 filed Feb. 16, 2022, which is based on and claims priority under 35 U.S.C. § 119 to U.S. Provisional Application No. 63/153,453 filed on Feb. 25, 2021, the entire contents of each of these applications is incorporated herein by reference.

FIELD OF DISCLOSURE

The present invention relates generally to stent devices and, in particular, to a stent device having a stent cover with porous and nonporous portions, which contributes to maintaining the stent devices effectiveness over a long period of time after placement in a patient's body. The calculated placement of the porous and nonporous portions of the cover provides variations of positive effects to the stent and the patient the stent is placed.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

In general, stent devices are implanted in the internal organs of a patient so as to push the lesion site and widen the stenosed organ such as bile duct, esophagus, and intestines. Stent devices may be covered or uncovered. On the one hand, in uncovered stent devices, restenosis may occur after implantation as lumen cells enter the stent lumen through the mesh of wires ("ingrowth"). While restenosis which may help to anchor a stent device and prevent the uncovered stent device from migration, i.e., shifting its position within the patient, restenosis may lead to a return of or new unwanted medical conditions, such as hyperplasia of lumen tissue into the inner luminal side of the stent body. On the other hand, as a measure against restenosis, covered stent devices may be used. But while the cover of covered stent devices prevents restenosis, the cover also prevents ingrowth resulting in the covered stent device not being anchored and subject to migration.

FIG. 13 is a figure of a stent device disclosed in the related art (U.S. Pat. App. Pub. No. 2002/0143384A1). FIG. 13 is a perspective view showing a cylindrical stent body 15 constructed by connecting plural elastic wire members 16 to each other, the wires 16 are bent in a spiral shape, and cutout parts are constituted by clearance between each wire members.

FIG. 14 is a figure from the same related art disclosing a stent 1 including a stent cover 100 with portions of the stent body 2 protruding out from the stent cover 100. The stent cover 100 is comprised of porous film end parts 3, nonporous film central part 5, and a joint part 4 where the porous film end parts 3 and nonporous film central part 5 overlap each other.

FIG. 15A is a cross-sectional view along the line 20-20 in FIG. 14 disclosing the inner and outer side surfaces of the stent body 2 of stent 1 covered by nonporous film central part 5. FIG. 15B is the cross-sectional view along the line 30-30 in FIG. 14 disclosing the inner and outer side surfaces of the stent body 2 of stent 1 covered by porous film central part 3. The porous film end parts 3 are intended to behave as a good anchorage for promoting endothelialization of the stent 1. On the other hand, the nonporous film central part 5 has low water permeability, whereby cellular infiltration from the body duct to inner luminal side of the stent body can be prevented and growth and hyperplasia of a lumen tissue into the inner luminal side of the stent body, resulting in blockage of the inner luminal side of the stent body can be prevented.

While conventional covered stent devices have a porous film stent cover at the end portions of the stent body, such conventional covered stent devices result in only the end portions of the stent body being available for restenosis and may not be sufficient to prevent effects such as stent displacement.

SUMMARY

Accordingly, there is a need for designing a stent device with an efficient structure in view of the practical usage, which would substantially obviate one or more of the issues due to limitations and disadvantages of related art stent device. An object of the present disclosure is to provide an improved stent device having an efficient structure and practical administration of the associated medical procedure. Additionally, there is a need for an improved covered stent device that balances the risks of restenosis and migration while allowing the stent device to serve its purpose of widening the stenosed organ at the treating portion. At least one or some of the objectives is achieved by the stent device disclosed herein.

For example, the disclosed stent device includes a stent cover having porous film portions throughout the stent body for promoting endothelialization to serve as anchoring sites for the stent device. In one aspect, the stent cover of the disclosed covered stent device is a film incorporating first regions and second regions of different affinity for endothelialization. For example, first regions of the film are nonporous (or of low porosity) which minimizes and/or prevents growth and hyperplasia of lumen tissues and covers the stent device in areas in order to prevent lumen tissues protruding into the inner luminal side of the stent body and, for example, cause clogging of the stent device, while second regions of the film are porous for promoting restenosis sufficient for anchoring and to prevent migration. In some aspects, the second regions of porous film correspond in location to the wire structure of the stent body and the first regions of the nonporous film correspond in location to the void spaces between the wire structure, e.g., the open cell portions of the stent body circumferential surface, with each open cell having a perimeter defined by the wire of the wire structure of the stent body. As such, endothelialization is directed to the location of the wire structure where anchoring can be established while endothelialization is minimized and/or prevented in locations without the wire structure and in which endothelialization would result in tissue intrusion into the inner luminal side of the stent body, but would otherwise only minimal contribute or not contribute to anchoring the stent device.

In general, the disclosed structures and systems provide for a stent and stent cover efficiently suppressing problems such as stent migration and ingrowth discussed above and in relation with the related art. To address the issues, a structure where a stent cover having a higher porosity ratio covering the stent wires and a stent cover having a lower porosity ratio (optionally no porosity) covering the stent open cell portion of the stent is disclosed. The stent cover with higher porosity ratio near the stent wires would allow the lumen tissues to penetrate into the stent cover and associate itself with the stent wires, resulting in endothelialization that helps prevent stent migration. The stent cover with lower porosity ratio covering the stent cell would prevent the ingrowth, resulting in prevention of clogging of the inner lumen of the stent device. The porosity ratio of the stent cover may be adjusted in various ways to adjust to needs caused by the condition of the lumens and other patient needs, including continuous and non-continuous gradients in porosity as a function of longitudinal position along the stent device or patterns of different porosities arranged at longitudinal position along the stent device.

Embodiments of the disclosed stent device comprises one or more stent wires forming a cylindrical stent body, the cylindrical stent body encloses an interior void space and defines an inner luminal side of the stent body, and a stent cover covering the cylindrical stent body. The one or more stent wires of the cylindrical stent body form a plurality of open cells in which each open cell incudes a perimeter defined by stent wire and enclosing a cell void space The stent cover includes one or more low porosity regions and one or more high porosity regions and the low porosity regions of the stent cover correspond in location to the open cells, and the high porosity regions correspond in location to the one or more stent wires.

Embodiments of the disclosed stent device further comprises the area the open cell is not covered by the low porosity portion is covered by the high porosity portion.

Embodiments of the disclosed stent device further comprises the ratio of the area the open cell is covered by the low porosity portion differs for at least one set of open cells.

Embodiments of the disclosed stent device further comprises the ratio of the area the open cell is covered by the low porosity portion is higher at the open cells located at the cylindrical center compared to the open cells located at the cylindrical end of the stent cover.

Embodiments of the disclosed stent device further comprises the ratio of the area the open cell is covered by the low porosity portion is higher at one half of the semi-cylinder compared to the other half of the semi-cylinder of the stent cover.

Embodiments of the disclosed stent device further comprises the stent cover not reaching both cylindrical ends of the cylindrical stent body.

Embodiments of the disclosed stent device further comprises the area the open cell being covered by the low porosity portion is zero for open cells located at the cylindrical end.

Embodiments of the disclosed stent device further comprises the area the open cell being covered by the low porosity portion has a circular shape.

Embodiments of the disclosed stent device further comprises the cylindrical stent body comprised of stent wires interlocking with each other through bent portions.

Embodiments of the disclosed stent device further comprises the stent cover comprised of an outer cover covering the cylindrical stent body from outside and an inner cover covering the cylindrical stent body from inside.

Embodiments of the disclosed stent device further comprises the outer cover having a higher porosity ratio compared to the inner cover.

Embodiments of the disclosed stent device further comprises a stent delivery system comprising a tip, a stent device, a double layered sheath carrying the stent device in between the layers, and a handle for removing the stent device from the sheath. The stent device has one or more stent wires forming a cylindrical stent body, enclosing an interior void space, defines an inner luminal side of the stent body, and covered by a stent cover. The one or more stent wires of the cylindrical stent body form a plurality of open cells in which each open cell incudes a perimeter defined by stent wire and enclosing a cell void space. The stent cover includes one or more low porosity regions and one or more high porosity regions, and the low porosity regions of the stent cover correspond in location to the open cells and the high porosity regions correspond in location to the one or more stent wires.

Embodiments of the disclosed stent delivery system further comprises an area the open cell is not covered by the low porosity portion being covered by the high porosity portion.

Embodiments of the disclosed stent device further comprises the ratio of the area the open cell is covered by the low porosity portion differs for at least one set of open cells.

Embodiments of the disclosed stent device further comprises the ratio of the area the open cell being covered by the low porosity portion is higher at the open cells located at the cylindrical center compared to the open cells located at the cylindrical end of the stent cover.

Embodiments of the disclosed stent device further comprises the ratio of the area the open cell being covered by the low porosity portion is higher at one half of the semi-cylinder compared to the other half of the semi-cylinder of the stent cover.

Embodiments of the disclosed stent device further comprises the stent cover not reaching both cylindrical ends of the cylindrical stent body.

Embodiments of the disclosed stent device further comprises the ratio of the area the open cell being covered by the low porosity portion is zero for open cells located at the cylindrical end.

Embodiments of the disclosed stent device further comprises the area the open cell being covered by the low porosity portion has a circular shape.

Embodiments of the disclosed stent device further comprises the cylindrical stent body being comprised of stent wires interlocking with each other through bent portions.

Embodiments of the disclosed stent device further comprises the stent cover being comprised of an outer cover covering the cylindrical stent body from outside and an inner cover covering the cylindrical stent body from inside.

Embodiments of the disclosed stent device further comprises the outer cover having a higher porosity ratio compared to the inner cover.

The term "patient," as used herein, comprises any and all organisms and includes the term "subject." A patient can be a human or an animal.

Additional features and advantages will be set forth in the description that follows, and in part will be apparent from the description, or may be learned by practice of the invention. The objectives and other advantages of the disclosed stent device will be realized and attained by the structure particularly pointed out in the written description and claims thereof, as well as the appended drawings.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed stent device as claimed.

BRIEF DESCRIPTION OF THE DRAWING

The following detailed description of preferred embodiments can be read in connection with the accompanying drawings in which like numerals designate like elements and in which:

FIGS. 15A and 15B shows the cross-sectional view of the related art stent device shown in FIG. 14.

Figure 1:
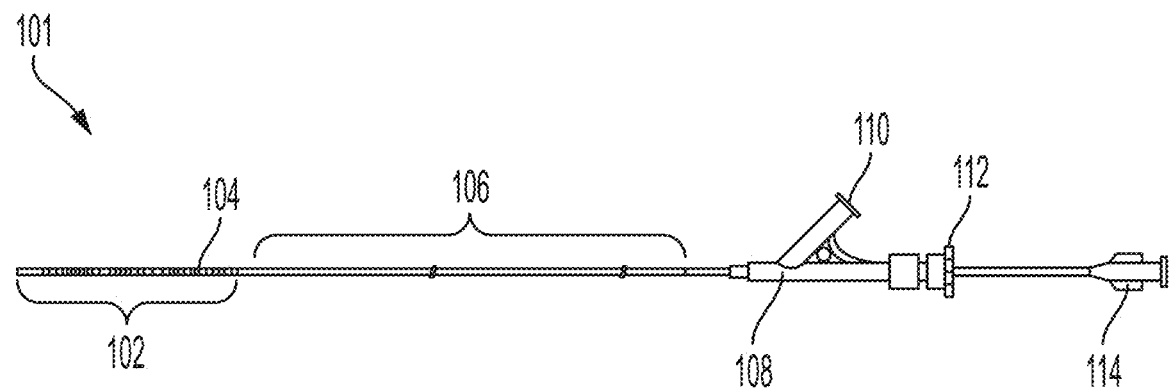
FIG. 1 shows an embodiment of a stent delivery system including the stent device.

Throughout all of the drawings, dimensions of respective constituent elements are appropriately adjusted for clarity. For ease of viewing, in some instances only some of the named features in the figures are labeled with reference numerals.

DETAILED DESCRIPTION

The following detailed description of preferred embodiments can be read in connection with the accompanying drawings in which like numerals designate like elements and in which: FIG. 1 is an illustration of a stent device delivering system 101. Stent delivery system 101 is comprised of tip portion 102, the stent device 104, sheath 106, two port hub 108, side port 110, rotatable handle lock 112, inner handle 114. The sheath 106 has a two-layered structure with inner sheath and outer sheath, having the stent device 104 in a reduced diameter held between the two layers at the tip portion 102. The tip portion 102 is connected to the inner sheath and the inner handle 114. The outer sheath is connected to the two port hub 108 and rotatable handle lock 112. After the stent delivery system 101 places the tip portion 102 and the stent device 104 to the desired position, by fixing the inner handle 110 and pulling the rotatable handle lock 112 toward the proximal side of the delivery system 101, the outer sheath at the tip portion 102 slides toward the proximal side, causing the stent device 104 to self-expand from the reduced diameter to the designed diameter. After the outer sheath finishes sliding the entire length of the stent device 104, the delivery system 101 and the stent device 104 are separated, leaving the stent device 104 to be implanted in the patient's body.

There are procedures that only use the stent delivery system 101 to implant the stent device 104 into the patient's body to open stenosis (e.g., vascular (circulatory) stents) and procedures that is combined with the use of an endoscope. In case for implanting bile duct stents, the endoscope is inserted through the mouth and advanced to the duodenum. Then the stent delivery system 101 is inserted through the forceps channel of the endoscope and through the duodenal papilla into the bile duct. Finally, the stent device 104 is placed in the bile duct stenosis with supports from visual feeds from the endoscope.

Figure 2A:
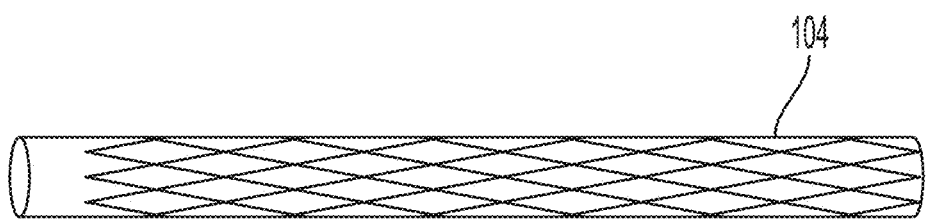
FIGS. 2A and 2B show schematic views of the stent body in a collapsed state (FIG. 2A) and an expanded state (FIG. 2B).
Figure 2B:
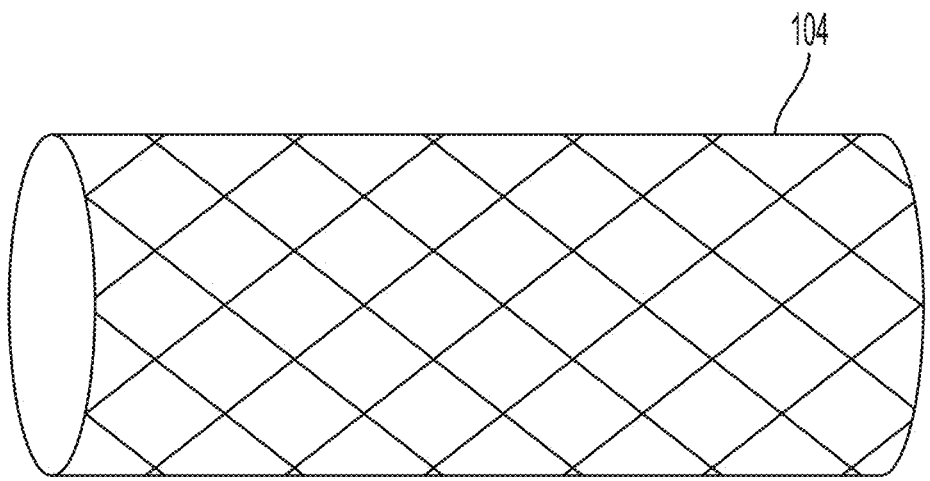

FIG. 2A is an illustration of the stent device 104 in its contracted state. The stent device is inserted into the stent delivery system 101 in the contracted state in order for the delivery of the stent device 104 to occur through blood vessels of the patient and other narrow space. As disclosed in FIG. 2B, after the stent device 104 reaches the treating portion and pushed out from the stent delivery system 101, the stent device 104 expands into the size it was designed for conducting treatment to the treating portion.

Figure 3:
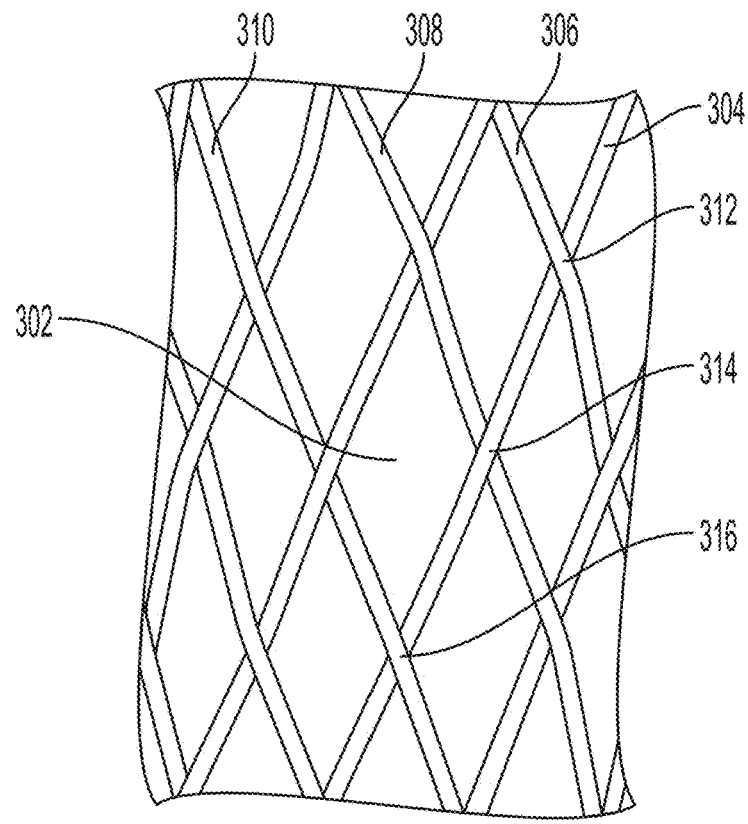
FIGS. 3 and 4 are magnified views of the stent wires in exemplary embodiments of a stent body.

FIG. 3 illustrates a pattern of the stent wires comprising the stent device 104. As disclosed in FIG. 3, the stent wires of the stent device 104 interchangeably cross over each other and form cells enclosed by the stent wires, such as stent cell 302. The state of interchange of the stent wires can be seen by looking closely at stent wires 304, 306, 308, and 310. The stent wire 304 intersects with stent wire 306 at intersection 312 where stent wire 304 submerges under stent wire 306. The stent wire 304 then intersects with stent wire 308 at intersection 314 where stent wire 304 comes over stent wire 308, and then submerges again under stent wire 310 at the next intersection 316. Thus, stent wire 304 intersects interchangeably with other stent wires.

Figure 4:
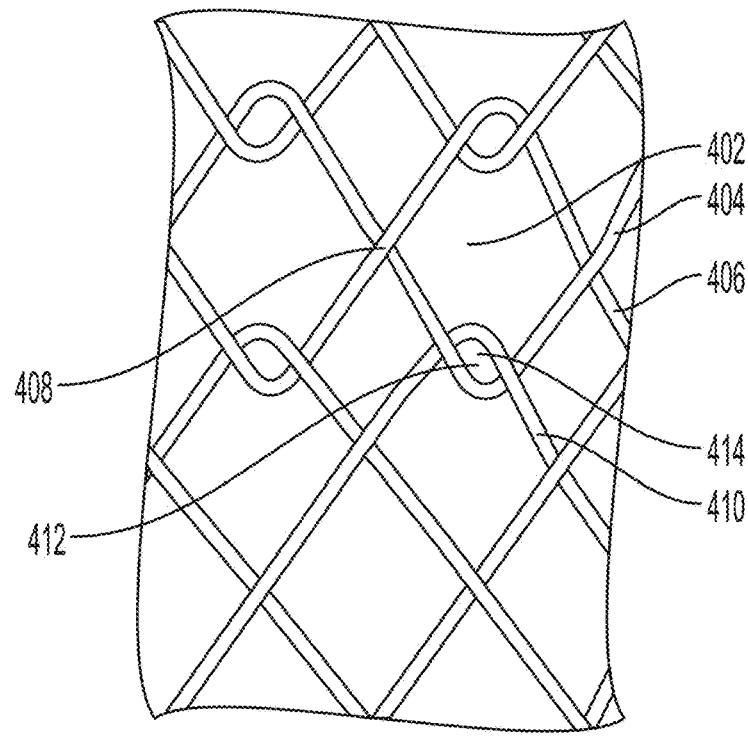

FIG. 4 illustrates another pattern of the stent wires comprising the stent device 104. As with FIG. 3, the stent wires of the stent device 104 interchangeably cross over each other and form cells enclosed by the stent wires, such as stent cell 402. The state of interchange disclosed in FIG. 4 is more complex compared to that in FIG. 3. For example, the stent wires 404 and 406 are interchangeably bend and cross over at intersection 408. The bent stent wires, such as stent wires 404 and 410, forms an interlocking intersection 412, which forms an interlocking stent cell 414.

Figure 5A:
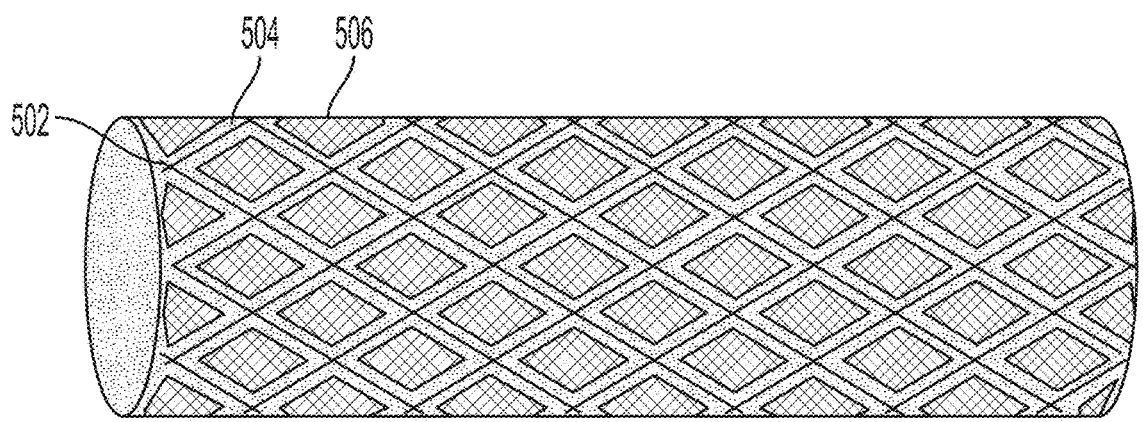
FIGS. 5A-C and 6A-B are schematic views of stent devices including embodiments of a stent cover having regions of varying porosity ratios at different locations of the stent body.

FIG. 5A is an illustration of a stent device 104 with a stent cover covering the entirety of the stent body. The stent wires of the stent device 104 (e.g. stent wire 502) intersects with other stent wires to form numerous stent cells enclosed by the stent wires. The stent cover covering the stent device 104 is comprised of two portions, namely the wire covering portion (e.g. 504) and the cell covering portion (e.g. 506), and the porosity ratio of the wire covering portion 504 and cell covering portion 506 may differ from each other.

For example, in case the porosity ratio of the wire covering portion 504 is higher (i.e. more pores), the pores near the stent wires would allow growth and hyperplasia of lumen tissues into the inner luminal side of the stent and associate itself with the stent wires, thereby providing good anchorage for promoting endothelialization throughout the body of stent 104 where the wire covering portion 502 exists. On the other hand, the lower porosity ratio (i.e. less pores) of the cell covering portion 506 will result in low water permeability and prevention of cellular infiltration from the body duct to inner luminal side of the stent, thereby preventing growth and hyperplasia of a lumen tissue into the cell portion of the stent body. The opposite structure, wherein the wire covering portion 504 has lower porosity ratio compared to cell covering portion 506 may also serve the purposes of promoting endothelialization and prevention of cellular infiltration of stent device 104, but may be less effective since the penetrating lumen tissues may not associate itself with the stent wires 502, the association serving to strengthen the endothelialization of the stent device 104.

The pore size of the cell covering portion may be less than 6 μm to prevent lumen cells from entering the inner lumens of the stent device. The pore size of the wire covering portion may be between 6 μm to 25 μm. Any material that is biocompatible may be suitable for the material of the stent cover, such as silicone-based resins, polyurethane-based resins, nylon-based resins, polyester-based resins, polyolefin-based resins such as polypropylene and polypropylene, and fluorine-based resins such as polytetrafluoroethylene (PTFE) and tetrafluoroethylene vinyl ether copolymer (FEP).

As an example of a method of making the porosity, silicone-based resin, polyurethane-based resin, nylon-based resin, polyester-based resin, polyolefin-based resin, etc. are extracted by mixing a pore-forming agent and removing it with a solvent after molding, or by mixing a foaming agent to create pores. Forming methods can also be used. The porosity can be controlled by controlling the pore-forming agent and the foaming agent. In addition, PTFE materials can be stretched to form a porous structure, so-called ePTFE. The porosity of this ePTFE material can be freely changed by adjusting the stretching direction and the stretching amount. For example, it is possible to obtain a porous material with suitable characteristics, such as a material stretched in one direction and a biaxial stretching stretched in the vertical and horizontal directions.

The thickness of the stent cover is preferably 100 μm or less, more preferably 30 μm to 10 μm, for the purpose of withstanding ingrowth and for purposes of maintaining the flexibility of the stent device.

Figure 5B:
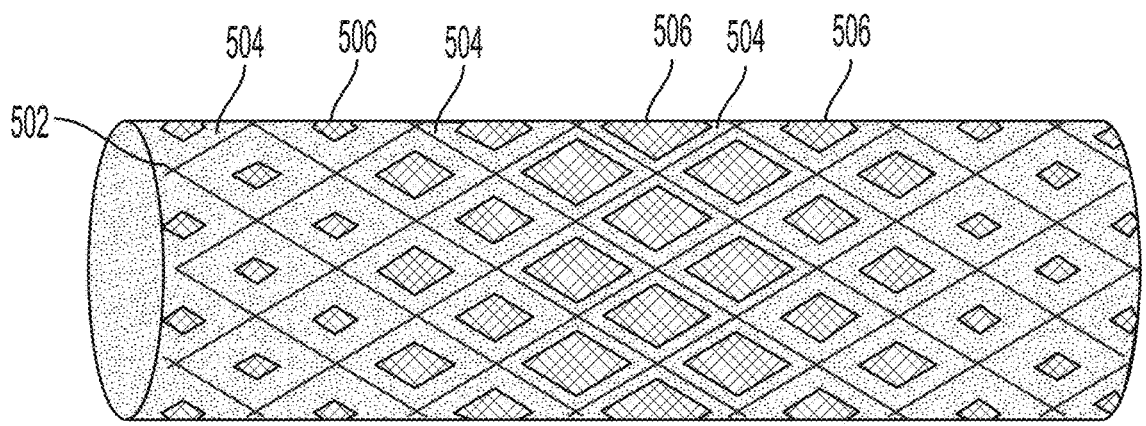

FIG. 5B is another illustration of a stent device 104 with a stent cover covering the entirety of the stent body. As with FIG. 5A, the wire covering portion 504 and the cell covering portion 506 may differ in their porosity rate. In case the porosity ratio of the wire covering portion 504 is higher, the pores near the stent wires would promote endothelialization and the lower porosity ratio of the cell covering portion 506 will result in less risk of clogging in the inner lumen portion of the stent body caused by the penetration of the lumen tissue into the cell portion of the stent body. The area of the wire covering portion 504 and cell covering portion 506 differs in accordance with the location of the wires and the cell. The area of the wire covering portion 504 are smaller at the center of the stent cover and becomes larger as the wire gets closer to the edge of the stent cover. On the contrary, the area of the cell covering portion 506 are larger at the center of the stent cover and becomes larger as the cell gets closer to the edge of the stent cover.

Figure 5C:
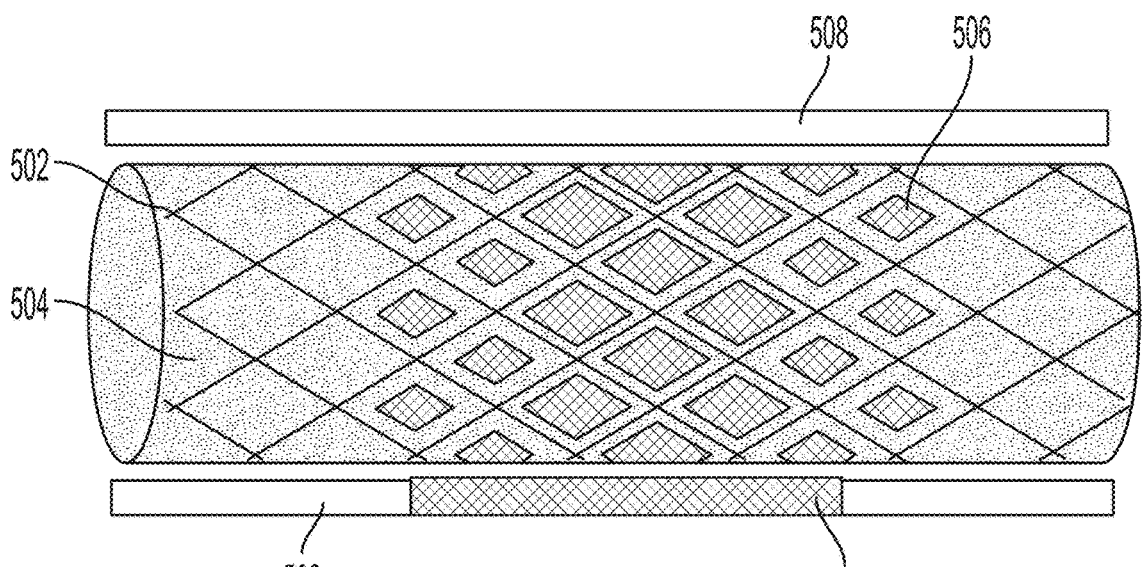

FIG. 5C is another illustration of a stent device 104 with a stent cover covering the entirety of the stent body having variations in the area of the wire covering portion 504 and cell covering portion 506. In FIG. 5C, the cell covering portion 506 does not exists near the edge of the stent cover and the entire cell is covered by the wire covering portion 504. This configuration and configuration in FIG. 5B is preferable due to the fact that stent device 104 is placed in the stenosed portion 508 of the patient's body with an aim to allocate the center part of the stent device 104 at the location where the focal of the treating portion 510 (e.g. cancer) in which the lumen tissues are likely concentrated. By placing the cell covering portion 506 having a lower porosity rate in the center part of the stent device 104, the ingrowth and risk of clogging of the inner lumen of the stent device is prevented. On the other hand, the wire covering portion 504 that is located at the edge portion of the stent device 104 promotes endothelialization that prevents migration of the stent device 104 from occurring.

Figure 6A:
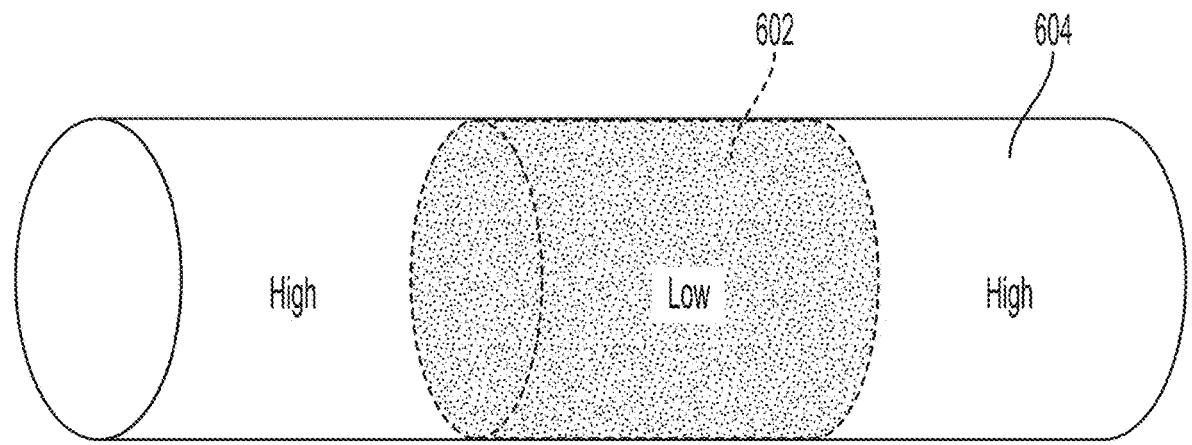

FIG. 6A is an illustration of the stent device 104 with the stent cover covering the entirety of the stent body having variations in the area of the wire covering portion 504 and cell covering portion 506. As with the embodiment disclosed in FIG. 5C, the center portion 602 of the stent cover has a relatively lower porosity ratio compared to the neighboring edge portion 604. The edge portion 604 having a relatively high porosity ratio serves as an anchor to hold the stent device 104 in place using the higher porosity ratio that promotes endothelialization. The center portion 602 serves to prevent penetration of the lumen tissue inside the stent body, which would cause clogging of the stent device. This configuration is effective, since the medical operator would aim to place the center portion 602 of the stent device directly on the focal of the treating portion where the lumen tissues are likely concentrated.

Figure 6B:
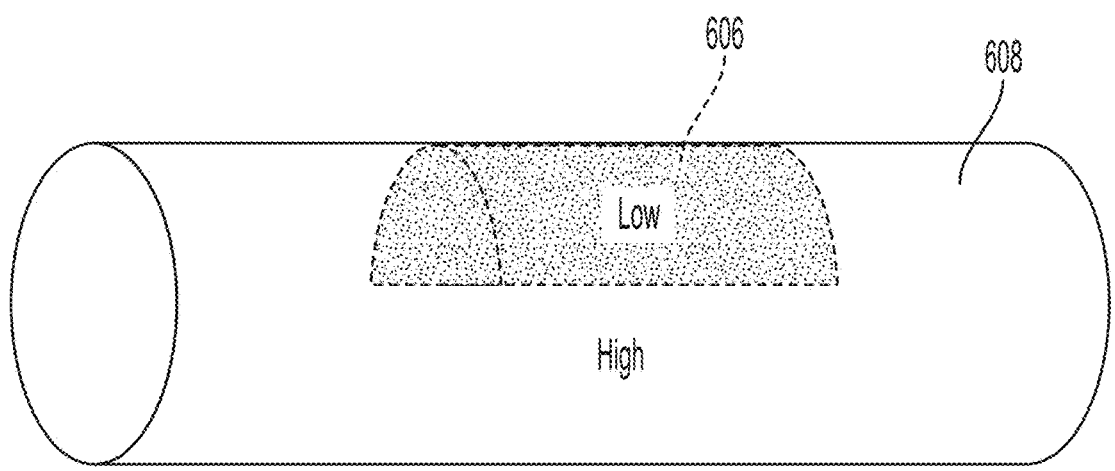

FIG. 6B is an illustration of the stent device 104 with the stent cover covering the entirety of the stent body having variations in the area of the wire covering portion 504 and cell covering portion 506. The center portion 606 of the stent cover has a semi-cylinder shape covering the upper half body of the center portion of the stent device 104. The remaining portion 608 of the stent cover covers the lower half body of the center portion of the stent device 104 and the area including the edge portion of the stent device 104. As in FIG. 6A, the center portion 606 has a relatively lower porosity ratio for preventing ingrowth and remaining portion 608 has a relatively higher porosity ratio for preventing migration of the stent device 104.

Figure 7A:
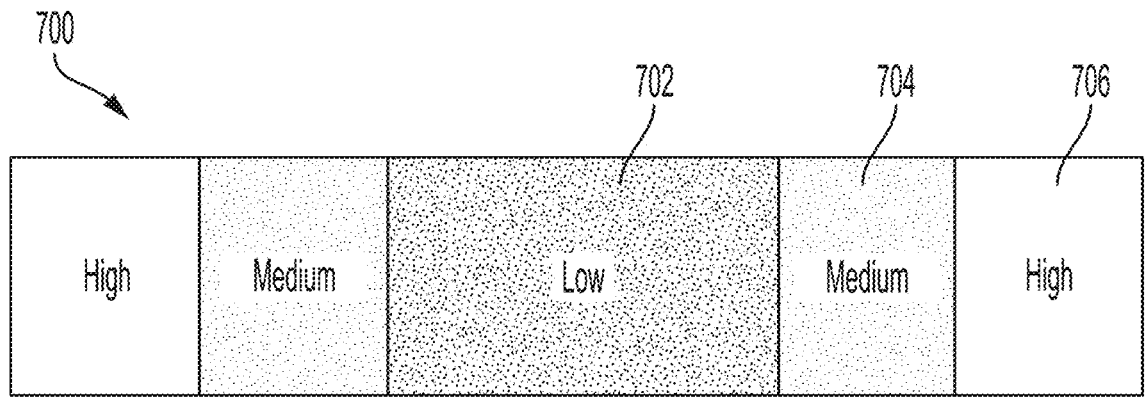
FIGS. 7A to 7C are schematic views of stent devices including other embodiments of a stent cover with portions with varying porosity ratios at different locations of the stent body.

FIG. 7A is an illustration of the stent cover 700 having varying porosity ratios based on the location. As with the embodiment disclosed in FIG. 6A, the center portion 702 of the stent cover 700 has a lower porosity ratio compared to the neighboring middle portion 704, and the middle portion 704 has an even lower porosity ratio compared to the neighboring edge portion 706. The edge portion 706 serves as an anchor to hold the stent device 104 in place using the high porosity ratio that promotes endothelialization. The center portion 702 serves to prevent ingrowth which would cause clogging of the stent device. This configuration is effective, since the medical operator would aim to place the center portion 702 of the stent device directly on the focal of the treating portion (e.g. cancer) where the lumen tissues are likely concentrated.

Figure 7B:
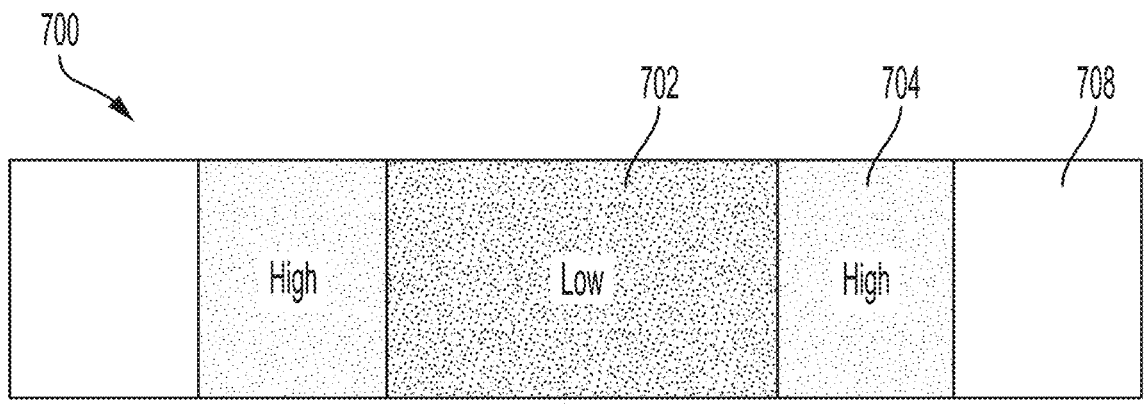

FIG. 7B is another illustration of the stent cover 700 having different porosity ratios. The center portion 702 of the stent cover 700 has a lower porosity ratio compared to the neighboring middle portion 704, and the stent cover 700 ends short of the edge of the stent device 104. The area lacking the stent cover 700 (i.e. area 708) serves as an even stronger anchor to hold the stent device 104 in place within the patient's treating portion by allowing lumen tissues to freely penetrate within the stent device 104 and associate with stent wires, promoting endothelialization.

Figure 7C:
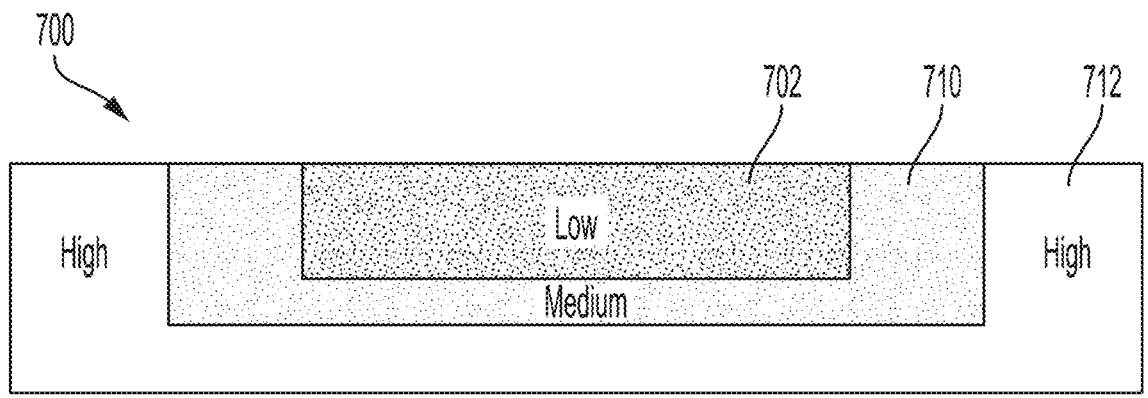

FIG. 7C is another illustration of the stent cover 700 having different porosity ratios. The center portion 702 of the stent cover 700 has a lower porosity ratio compared to the rest of the stent cover 700 (i.e. 710). The center portion 702 may be designed to optimize the location and size of the area in accordance with the lumen tissues it intends to cover. By aiming to allocate the stent cover portion with low porosity ratio to the exact location of the lumen tissues, the prevention of cellular infiltration of the stent device 104 may be minimized, and the endothelialization of the stent device 104 maximized by optimizing the stent cover portion with higher porosity ratios to cover the areas in the treating portion with less concentration of the lumen tissues.

Figure 8A:
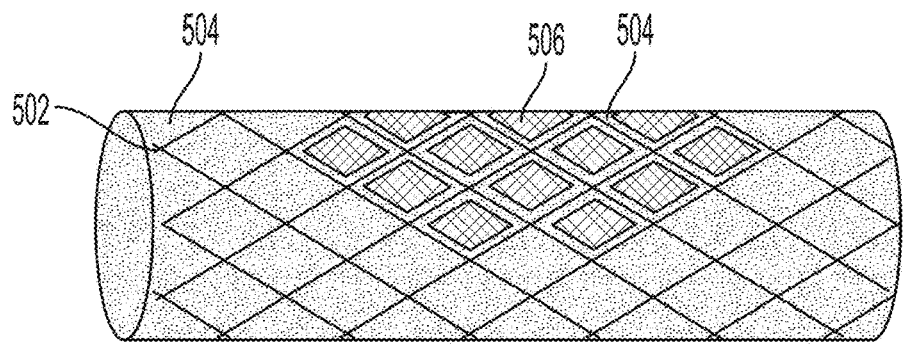
FIGS. 8A to 8D are schematic views showing embodiments of the structures of the stent wire and stent cover.
Figure 8B:
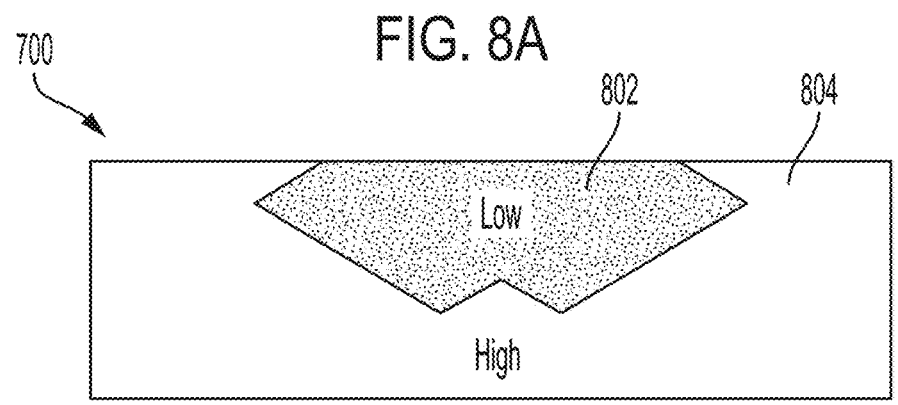

FIG. 8A is an illustration of the stent device 104 with another pattern of varying porosity ratios based on the location. As with the embodiment disclosed in FIG. 6B, the center portion of the stent cover 700 has the concentration of cell covering portion 506 on the upper side of the stent device 104 and remaining portion consisting of wire covering portion 504. FIG. 8B illustrates the relationship of the high porosity portion 804 and low porosity portion 802. The high porosity portion 804 is consisted mainly with cell covering portion 506 and the low porosity portion 802 is consisted entirely with wire covering portion 504.

Figure 8C:
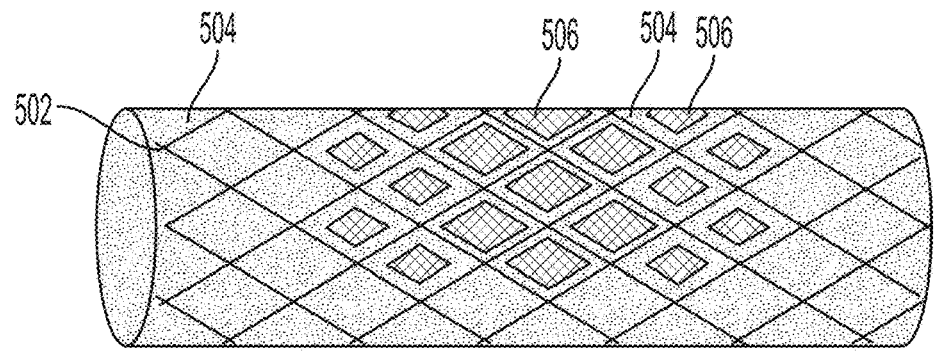
Figure 8D:
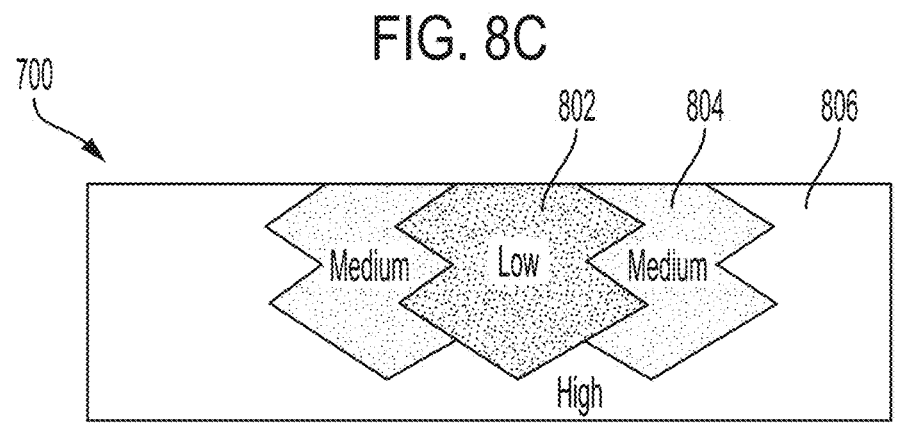

FIG. 8C is an illustration of the stent device 104 with another pattern of varying porosity ratios based on the location. As with the embodiment disclosed in FIG. 8A, the center portion of the stent cover 700 has the concentration of cell covering portion 506 on the upper side of the stent device 104 and remaining portion consisting of wire covering portion 504. The center portion of the stent cover 700 has varying concentration of cell covering portion 506, with the area covering each cell becoming larger towards the center of the stent device 104. FIG. 8D illustrates the relationship of the high porosity portion 806, medium porosity portion 804, and low porosity portion 802. The high porosity portion 806 is consisted mainly with cell covering portion 506, the medium porosity portion 804 is consisted with cell covering portion 506 with a smaller area covering the cell, and the low porosity portion 802 is consisted entirely with wire covering portion 504.

Figure 9A:
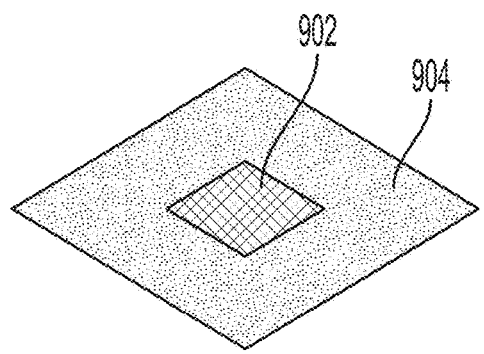
FIGS. 9A to 9D are schematic views showing embodiments of the structures of the stent wire and multiple stent covers.
Figure 9B:
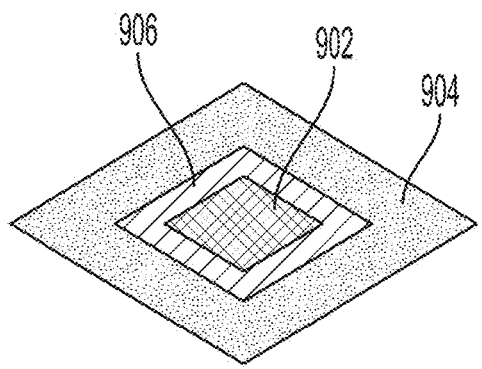

FIG. 9A is an illustration of the cell of the stent cover 700 having varying porosity ratios. The diamond shaped center portion 902 has a lower porosity ratio compared to the remaining portion 904 with a higher porosity ratio. FIG. 9B also discloses the diamond shaped center portion 902 having a lower porosity ratio compared to the remaining portion 904 and a medium porosity ratio portion 906 having a porosity ratio higher than the center portion 902 and lower than remaining portion 904 in between.

Figure 9C:
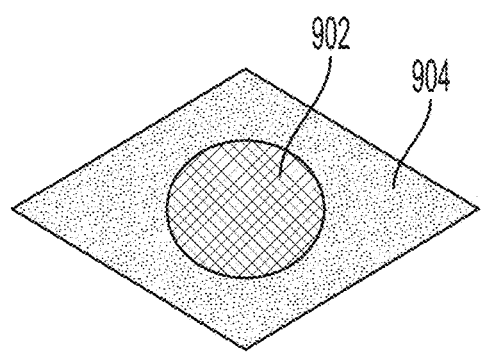
Figure 9D:
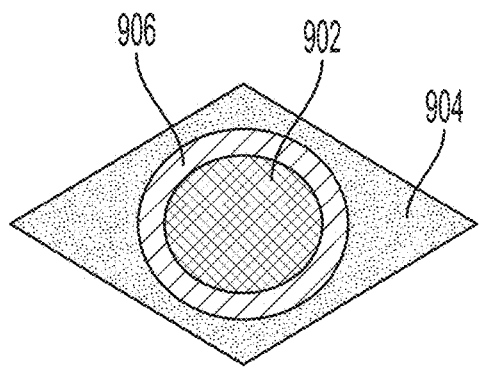

FIG. 9C is an illustration of the cell of the stent cover 700 having varying porosity ratios. The circular shaped center portion 902 has a lower porosity ratio compared to the remaining portion 904 with a higher porosity ratio. FIG. 9D also discloses the circular shaped center portion 902 having a lower porosity ratio compared to the remaining portion 904 and a medium porosity ratio portion 906 having a porosity ratio higher than the center portion 902 and lower than remaining portion 904 in between.

The stent covers with varying porosity can be manufactured by the following method. The material with a low porosity can be joined with an adhesive at the same time as the cover is joined by applying an adhesive to the part 902 shown in FIGS. 9A and 9C at a location where the porosity is desired to be reduced and the adhesive impregnates the porous part. Further, when the porosity is stepped as shown in FIGS. 9B and 9D, it can be manufactured by a joining method such as thermocompression bonding. The ePTFE material can be joined by crimping it above the melting point temperature, and by changing the pressing force of the joint, the degree of crushing of the stretched pore structure changes, and the porosity changes, as shown in FIGS. 9B and 9D.

Figure 10A:
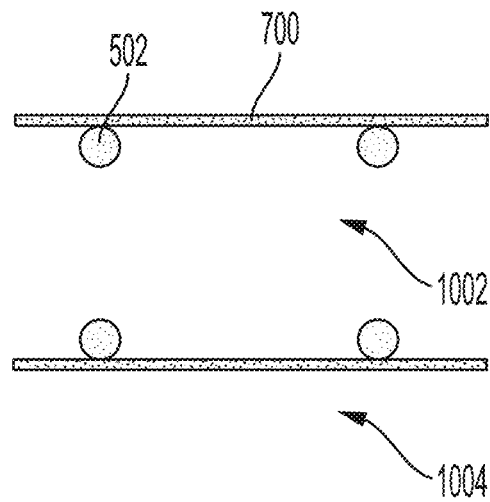
FIGS. 10A and 10B are schematic views showing embodiments of the structures of the stent wire and stent covers.
Figure 10B:
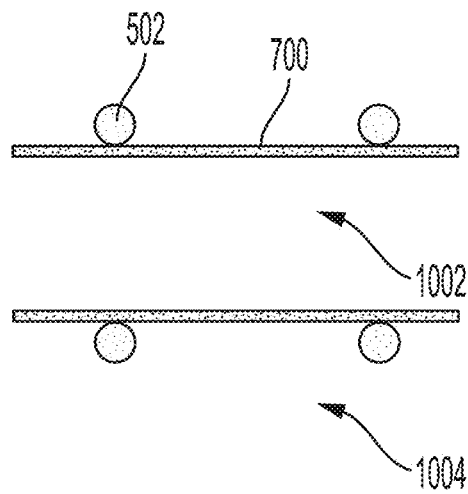

FIG. 10A is an illustration disclosing an embodiment of the structural relationship of the stent wires 502 and stent cover 700. As disclosed in FIG. 10A, the stent cover 700 covers the stent wires 502 of the stent device 104 at the outer lumen 1004 (i.e. from outside of the stent device 104). On the contrary, an embodiment disclosed in FIG. 10B shows the stent cover 700 covering the wires 502 of the stent device 104 at the inner lumen 1002 (i.e. from within the stent device 104).

Figure 11A:
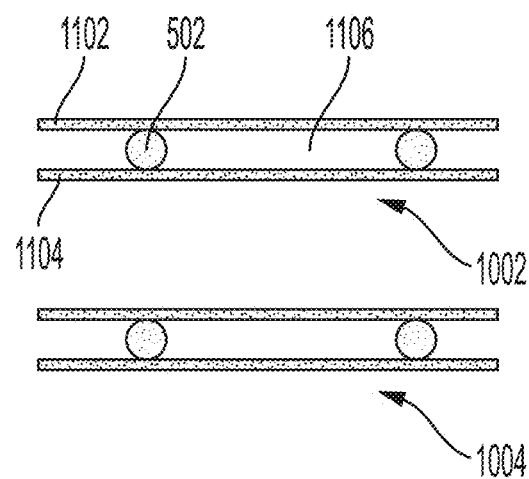
FIGS. 11A and 11B are schematic views showing embodiments of the structures of the stent wire and multiple stent covers.

FIG. 11A is an illustration disclosing an embodiment of the structural relationship of the wires of the stent device 104 and multiple stent covers. The stent cover 1102 covers the wires 502 of the stent device 104 at the outer lumen 1004. In addition, the stent cover 1104 covers the wires 502 of the stent device at the inner lumen 1002, forming a gap 1106.

Figure 11B:
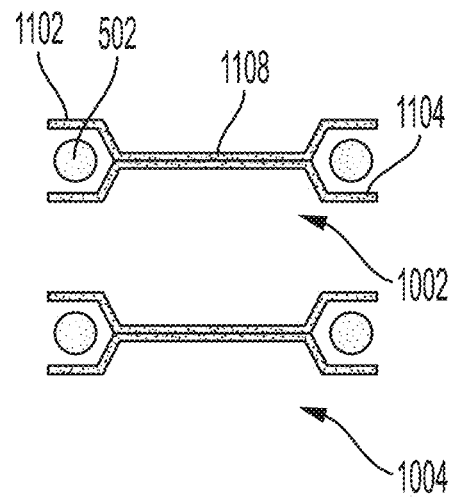

FIG. 11B is another illustration disclosing an embodiment of the structural relationship of the wires of the stent device 104 and multiple stent covers. As disclosed in FIG. 11A, the stent cover 1102 covers the wires 502 of the stent device 104 at the outer lumen 1004 and the stent cover 1104 covers the wires 502 at the inner lumen 1002. As opposed to FIG. 11A, the stent covers 1102 and 1104 adhere to each other at the location where wires 502 does not exist. The porosity ratio of the adhered portion 1108 would be lower than the individual stent covers 1102 and 1104, due to the overlap of the stent covers cancelling out the each other's pores. Therefore, the porosity ratio of the adhered portion 1108 would be lower compared to the stent covers covering the wire 502, namely the stent cover 1102 at the outer lumen 1004 and stent cover 1104 at the inner lumen 1002. In addition, the structure in FIG. 11B allows the stent to bend flexibly because the wires and covers are not directly fixed. Therefore, when the stent device 104 is implanted in the biological lumen in a bent state, the load on the biological lumen can be reduced.

Figure 12A:
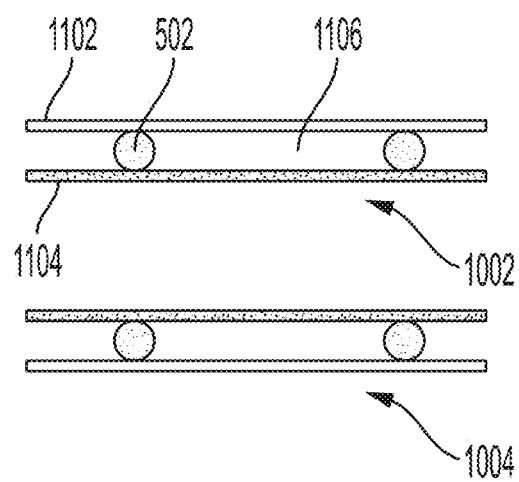
FIGS. 12A and 12B are schematic views showing embodiments of the structures of the stent wire and multiple stent covers having different porosity ratios.

FIG. 12A is an illustration disclosing another embodiment of the structural relationship of the wires of the stent device 104 and multiple stent covers. The stent cover 1102 covers the wires 502 at the outer lumen 1004 and the stent cover 1104 covers the wires 502 at the inner lumen 1002, forming a gap 1106. The porosity ratio of the stent cover 1102 and stent cover 1104 may be made different. For example, stent cover 1102 may have higher porosity compared to stent cover 1104, making it easier for the lumen tissues to penetrate into the stent cover 1102 and into the gap 1106, associating itself with stent wires 502 resulting in endothelialization. On the other hand, the penetration would be stopped at the stent cover 1104 having a lower porosity ratio, resulting in the inner lumen 1002 to be less affected with issues related to clogging.

Figure 12B:
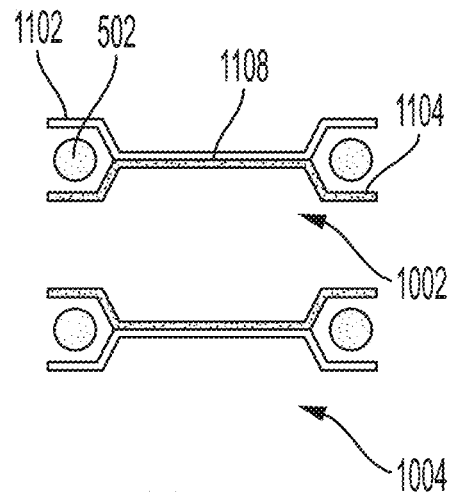
Figure 13:
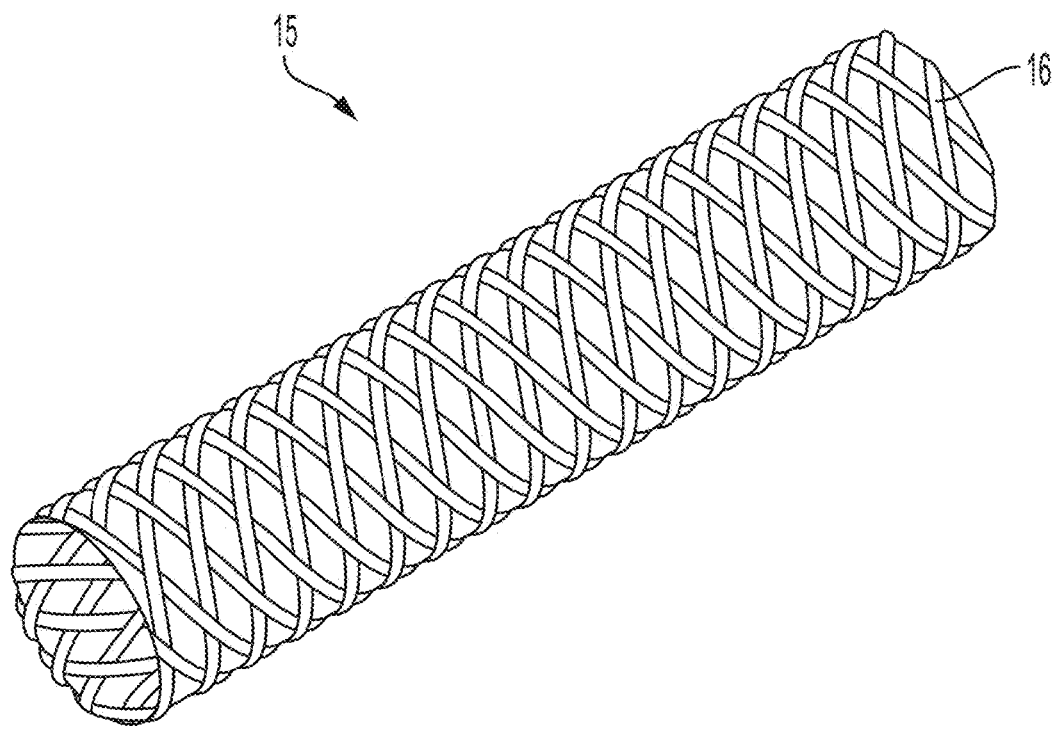
FIGS. 13 and 14 shows related art stent devices.
Figure 14:
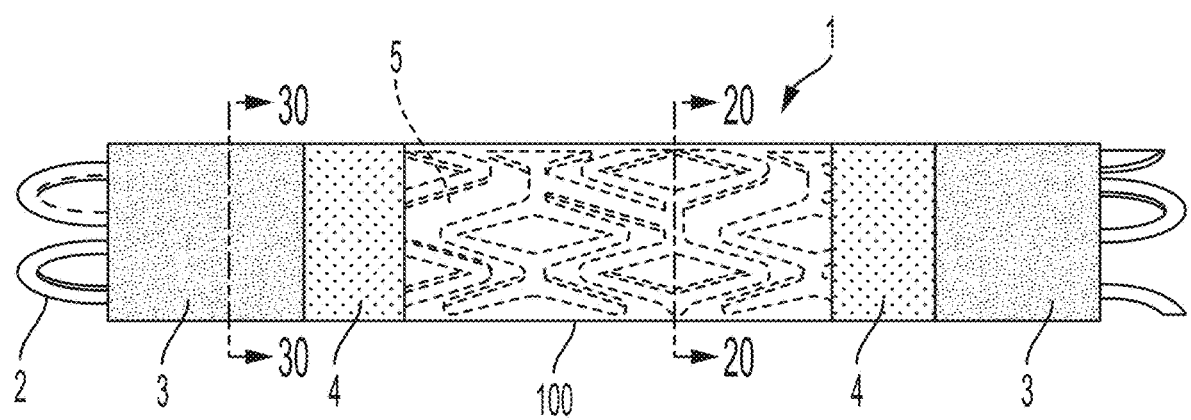

FIG. 12B is another illustration disclosing an embodiment of the structural relationship of the wires of the stent device 104 and multiple stent covers. As disclosed in FIG. 12A, the stent cover 1102 covers the stent wires 502 at the outer lumen 1004 and the stent cover 1104 covers the stent wires 502 at the inner lumen 1002. As opposed to FIG. 12A, the stent covers 1102 and 1104 adhere to each other at the location where stent wires 502 does not exist and form adhered portion 1108 having a lower porosity ratio effectively preventing the penetration of the lumen tissues into the inner lumen 1002.

The porosity ratio of the stent cover 1102 and stent cover 1104 may be made different. For example, stent cover 1102 may have higher porosity compared to stent cover 1104, easing the lumen tissues to penetrate into the stent cover 1102 and associate itself with stent wires 502, effectively promoting endothelialization. On the other hand, the penetration would be stopped at the adhered portion 1108 due to the low porosity ratio of the stent cover 1104, in addition to the lowered porosity ratio caused by the overlap of the two stent covers. The penetration would also be stopped at stent cover 1104 covering near the stent wires 502, resulting in the inner lumen 1002 to be less affected by the penetration of the lumen tissues compared to the case where stent cover 1104 has same porosity ratio as stent cover 1102.

The manufacturing method of a stent device 104 include, (i) weaving a wire of NiTi alloy (a superelastic alloy) to form a stent, (ii) wrapping biaxially stretched PTFE (pore diameter: 10 µm, thickness: 40 µm) around the outer surface of the cylindrical core material, placing the stent device over the cylindrical core material, and then wrapping biaxially stretched PTFE (pore diameter: 10 µm, thickness: 40 µm) around the stent device, (iii) using a soldering iron that is adjusted to be around 350° C., pressing the soldering iron against the central part of the mesh (cell) of the stent device to fuse and fix the PTFE on the outer and inner surfaces of the stent device, (iv) removing the stent device from the cylindrical core material. The area of the cells the soldering iron is applied to should be larger towards the cells located at the center of the stent device and smaller at towards both ends of the stent device.

The above manufacturing method is not limited to double-sided or two layered covered stents, but can also be used for covered stents with only one stent covers, at either outer or inner surfaces of the stent device, granted that the stent cover is fixed to the stent device through adhesion, string, or wiring. Since the porous ratio can be reduced at will using the soldering iron, the porous ration of each cells of the covered stents may be changed in accordance to the design and purpose of the covered stent.

The above manufacturing method is not limited to double-sided cover stents, but can also be used for cover stents with only the stent lumen surface or only the outer periphery surface, as long as the fixation to the stent is done by adhesion, string, or wire, the porous ratio can be reduced, and cover stents with any change in porous ratio can be manufactured.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A stent, comprising:
a body braided by one or more wires; and
a cover configured to cover at least part of the body,
wherein the body has a plurality of cells surrounded by the wires,
wherein one cell of the plurality of cells has a first area and a second area and a third area,
wherein the cover has a first portion and a second portion and a third portion, the first portion corresponding to the first area and the second portion corresponding to the second area and the third portion corresponding to the third area,
wherein the second portion is surrounded by the first portion,
wherein a porosity ratio of the first portion is higher than a porosity ratio of the second portion,
wherein a porosity ratio of the third portion is lower than the porosity ratio of the first portion, and
wherein the porosity ratio of the third portion is higher than the porosity ratio of the second portion.

2. The stent according to claim 1, wherein a shape of the second portion is similar in shape to the one cell.

3. The stent according to claim 1, wherein a shape of the second portion is circular.

4. The stent according to claim 1, wherein the first portion overlaps the one or more wires.

5. The stent according to claim 1, wherein the first portion is at a first distance relative to the one or more wires, the second portion is at a second distance relative to the one or more wires, and the first distance is less than the second distance.

6. The stent according to claim 1, wherein the first portion and the second portion are on a common plane.

7. The stent according to claim 1, wherein the third portion is located between the first portion and the second portion.

8. The stent according to claim 7, wherein the third portion is surrounded by the first portion.

9. The stent according to claim 7, wherein the second portion is surrounded by the third portion.

10. The stent according to claim 1, wherein the cover is a second cover,
wherein the stent further comprises a first cover, and
wherein the first cover is located outside the body and the second cover is located inside the body.

11. The stent according to claim 10, wherein the first cover and the second cover contact at the second portion.

12. The stent according to claim 10, wherein the first cover and the second cover are spaced apart at the first portion.

13. The stent according to claim 10, wherein a porosity ratio of the first cover is higher than the porosity ratio of the first portion.

14. The stent according to claim 10, wherein the first cover has a high porosity region and a low porosity region, and
wherein a porosity ratio of the high porosity region is higher than a porosity ratio of the low porosity region.

15. The stent according to claim 14, wherein the low porosity region and the second portion contact each other.

16. The stent according to claim 14, wherein the high porosity region and the first portion are spaced apart.

17. The stent according to claim 14, wherein the porosity ratio of the high porosity region is higher than the porosity ratio of the first portion.

18. A stent, comprising:
a body braided by one or more wires; and
a cover configured to cover at least part of the body,
wherein the body has a plurality of cells surrounded by the wires,
wherein the cover has one or more high porosity regions and one or more low porosity regions in an area where the cells are covered by the cover, and
wherein the one or more low porosity regions of the cover correspond in location to one or more of the cells, and the one or more high porosity regions of the cover correspond in location to the one or more wires.

19. The stent according to claim 18, wherein the cover is a second cover,
wherein the stent further comprises a first cover, and
wherein the first cover is located outside the body and the second cover is located inside the body.

20. The stent according to claim 19 wherein the first cover has a high porosity region and a low porosity region, and
wherein a porosity ratio of the high porosity region of the first cover is higher than a porosity ratio of the low porosity region of the first cover.

* * * * *